United States Patent [19]

Skuballa et al.

[11] 3,984,454

[45] Oct. 5, 1976

[54] CRYSTALLINE PROSTANOIC ACID ESTERS

[75] Inventors: Werner Skuballa; Bernd Raduchel; Helmut Vorbruggen; Walter Elger; Olaf Loge; Wolfgang Losert, all of Berlin, Germany

[73] Assignee: Schering Aktiengesellschaft, Berlin & Bergkamen, Germany

[22] Filed: May 2, 1974

[21] Appl. No.: 466,173

[30] Foreign Application Priority Data

May 3, 1973 Germany............................ 2322655

[52] U.S. Cl.......................... 260/468 D; 260/479 S; 260/514 D
[51] Int. Cl.$^2$....................................... C07C 177/00
[58] Field of Search............................... 260/468 D

[56] References Cited
UNITED STATES PATENTS

| | | | |
|---|---|---|---|
| 3,775,462 | 11/1973 | Axon .................................. | 260/468 |
| 3,823,180 | 7/1974 | Lincoln et al....................... | 260/468 |
| 3,836,578 | 9/1974 | Samuelsson........................ | 260/514 |
| 3,847,966 | 11/1974 | Pike.................................... | 260/468 |
| 3,856,852 | 1/1975 | Hsu et al............................ | 260/514 |

OTHER PUBLICATIONS

McOmie, Protective Groups, pp. 188, 196–207 (1973).

*Primary Examiner*—Robert Gerstl
*Attorney, Agent, or Firm*—Millen, Raptes & White

[57] ABSTRACT

Prostanoic acid esters of the formula $$PG - CH_2 - X - Y$$

wherein PG is the prostanoyloxy radical of a prostaglandin, X is a carbon-carbon single bond, carbonyl or carbonyloxy, and Y is substituted phenyl are easily crystallized compounds at least as active as the unesterified prostanoic acid and useful for the purification of the parent prostaglandin are prepared by reacting, in the presence of an agent which splits off hydrogen halide, the unesterified prostaglandin with a halide of the formula Hal—CH$_2$—X—Y, wherein Hal is a halogen atom and X and Y have the values given above.

12 Claims, No Drawings

CRYSTALLINE PROSTANOIC ACID ESTERS

BACKGROUND OF THE INVENTION

This invention relates to novel, easily crystallized prostanoic acid esters and to a process for their production.

Prostaglandins are known to be novel hormones having a wide activity spectrum. They are effective in small amounts as vasodilatory agents and bronchodilators, they affect fat metabolism and they are utilized as agents for initiating abortion and for inducing labor.

German Unexamined Laid-Open Applications DOS 2,155,546, 2,159,509 and 2,117,188 disclose prostaglandin esters showing a better effectiveness than the free acids. The essential disadvantage of these esters resides in that they are in most cases oily or difficult-to-crystallize compounds, so that they can be purified only under great difficulties. Moreover, complicated processes are required for their preparation. Thus, after converting the prostanoic acids into a tertiary amine salt, a mixed anhydride is first prepared, in DOS 2,155,546 with a pivaloyl halogenide, and in DOS 2,159,509 with an alkyl or phenyl sulfonyl halogenide, and this anhydride is then reacted with an alcohol to produce the prostaglandin ester.

It has now been found that by reacting prostanoic acids with certain halogen compounds as defined hereinafter, crystalline prostanoic acid esters having the same or superior activity compared to the corresponding free acid are obtained in good yields in a single stage.

SUMMARY OF THE INVENTION

According to this invention, novel crystalline prostanoic acid esters of the general formula I $$PG - CH_2 - X - Y \qquad \text{I}$$

wherein PG is the prostanoyloxy radical of a natural prostanoic acid prostaglandin or of a synthetic prostanoic acid analog of a prostaglandin, X is a direct carbon-carbon single bond, carbonyl (—CO—) or carbonyloxy (—COO—) and Y is a substituted phenyl ring, are produced by reacting a natural prostanoic acid prostaglandin or a synthetic prostanoic acid analog thereof, in the presence of an agent which splits off hydrogen halide, with a halogen compound of the general Formula II $$Hal - CH_2 - X - Y \qquad \text{II}$$

wherein Hal is a halogen atom, preferably bromine, and X and Y have the values given above.

DETAILED DISCUSSION

The term "natural prostaglandins" means the prostaglandins occurring in nature bearing a free carboxylic acid group, preferably prostaglandin $A_1$, $A_2$, $E_1$, $E_2$, $E_3$, $F_{1\alpha}$, $F_{2\alpha}$, $F_{3\alpha}$, $B_1$ and $B_2$. The term "known analogs" means prostaglandin derivatives known in the literature having the acid group of the natural prostaglandins, such as, for example, 19-oxaprostaglandin $F_{2\alpha}$, 13,14-dihydro-prostaglandin $E_1$, 13,14-dihydro-prostaglandin $E_2$ and 13,14-dihydroprostaglandin $F_{2\alpha}$.

These starting prostaglandins are all characterized by possessing an esterifiable —COOH group. They all possess the following basic prostanoyloxy (PG) structure:

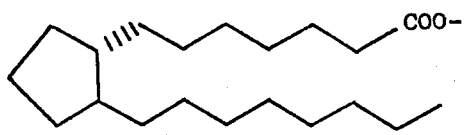

Examples of functional groups which may be present are an oxygen function (keto or hydroxy) in the 9- and 15-positions, an hydroxy group in the 11-position, one or more double bonds, e.g., at $C_5$, $C_{11}$, $C_{13}$ and/or $C_{17}$.

The esterifying groups are benzyl, phenacyl and phenoxycarbonylmethyl bearing at least one substituent, e.g., 1 or 2, on the phenyl ring.

Preferred phenyl ring substituents are phenyl, alkoxy, e.g., of 1–2 carbon atoms, and halogen atom, e.g., a bromine atom, especially in the p-position.

Examples of suitable agents which split off hydrogen halide are silver oxide, $Na_2CO_3$, $K_2CO_3$, $NaHCO_3$, $CaCO_3$, $KHCO_3$ and amines, preferably tertiary amines, for example, trialkylamines, e.g., triethylamine, trimethylamine, tributylamine, trioctylamine and heterocyclic aromatic tertiary amines, e.g., pyridine as well as alkali and alkaline earth hydroxides. Hal can be Cl, Br or I.

The reaction is conducted in an inert solvent, preferably in acetone, acetonitrile, dimethylacetamide, dimethylformamide, or dimethyl sulfoxide, and preferably at room temperature, although a wide temperature range, e.g., $-80°$ C. to $+10°$ C, can be employed. Also two-phase systems, e.g., $CHCl_2/H_2O$ can be used.

It was surprising that unstable and sensitive prostanoic acids could be esterified, with a simple apparatus and in a single stage, in an almost quantitative yield to produce valuable crystalline esters without decomposition of the starting material.

The novel prostanoic acid esters are distinguished by their excellent crystallization properties. For this reason, the purification of these esters causes no difficulties whatever, in contrast to the oily starting materials. Furthermore, they possess excellent stability. They can be stored at room temperature over a rather long period of time without decomposition, in contrast to the free prostanoic acids and the theretofore known esters.

The prostanoic acid esters are valuable pharmaceuticals, since they show, with the same spectrum of effectiveness, a substantially potentiated and especially prolonged effectiveness as compared to the starting acids.

Several of the compounds have shown good abortive properties in an in vivo test. Gravid rats were treated with the prostaglandin esters from the 4th to the 7th day of pregnancy. The animals were sacrificed on the 9th day and the uteri examined for locations of implantation.

In these tests, the esters of prostaglandin $F_{2\alpha}$ and of the prostaglandins of the E-type of this invention were abortively effective at minimum effective dosages which were one-third to one-tenth those of the corresponding free prostaglandins.

Thus, for example, the following novel prostaglandin esters are more effective than natural prostaglandin $F_{2\alpha}$ by the factor n, i.e., to trigger abortion, 1/n mg. of the test compound is required.

---

| | |
|---|---|
| prostaglandin-$F_{2\alpha}$ | n = 1 |

| | |
|---|---|
| prostaglandin-$F_{2\alpha}$ -p-bromophenacyl ester | n = 3 |
| prostaglandin-$F_{2\alpha}$ -p-phenylbenzyl ester | n = 10 |
| prostaglandin-$F_{2\alpha}$ -2,5-dimethoxyphenacyl ester | n = 10 |
| prostaglandin-$F_{2\alpha}$ -p-phenylphenacyl ester | n = 3 |

The esters of the present invention affect the uterine musculature in a manner typical of the free prostanoic acid. The PG-E-esters particularly show, on the isolated rabbit trachea, pronounced in vitro bronchodilatory effect. They also strongly inhibit the gastric secretion, and exert a regulating effect in case of heart rhythm irregularities (arrythmia). The PG-E- and PG-A-esters also lower blood pressure and have a diuretic effect.

Another advantage of the process of this invention is that the ester group can be readily split off in an almost quantitative manner to regenerate the starting prostanoic acid. This provides an excellent process for the purification of impure natural prostaglandins and known analogs by forming therefrom a prostanoic acid ester of general Formula I, purifying the thus-produced ester, and thereafter splitting off the ester group to regenerate the thus-purified starting prostaglandin.

The splitting-off of the ester group can be conducted according to generally know methods but preferably by reaction with zinc dust in glacial acetic acid (Tetrahedron Letters, 1970, 343).

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

Prostaglandin $E_2$-(p-Biphenylyloxycarbonylmethyl) Ester 100 mg. of prostaglandin $E_2$, 40 mg. of silver oxide, 90 mg. of p-phenyl-phenol bromoacetate are agitated in 2 ml. of dimethylacetamide overnight at room temperature. The mixture is diluted with ether, the solution is shaken three times with saturated NaCl solution, and evaporated to dryness under vacuum. The residue is filtered over a silica gel column with 30 g. of silica gel, a hexane/ethyl acetate mixture (1:2) being used for elution. Yield: 95 mg. of crystalline ester, m.p. 80°–81° C. (from hexane/ethyl acetate).

EXAMPLE 2

Prostaglandin $F_{2\alpha}$ -p-Phenylbenzyl Ester 100 mg. of prostaglandin $F_{2\alpha}$, 40 mg. of silver oxide, 85 mg. of p-phenylbenzyl bromide are agitated overnight in 2 ml. of dimethylformamide, at room temperature. The reaction mixture is worked up and purified as described in Example 1. Yield: 85 mg. of ester, m.p. 83°–85° C. (from hexane/ethyl acetate).

EXAMPLE 3

Prostaglandin $F_{2\alpha}$ -p-Bromophenacyl Ester 105 mg. of prostaglandin $F_{2\alpha}$., 33 mg. of triethylamine, 92 mg. of p-bromophenacyl bromide are agitated overnight at room temperature in 4 ml. of acetone. The mixture is then diluted with ether, shaken twice with saturated NaCl solution, dried and evaporated to dryness under vacuum. The residue is purified as set forth in Example 1. Yield: 119 mg. of crystalline ester, m.p. 95°–96° C. (from hexane/ethyl acetate).

Following the procedures of Examples 1–3, the p-phenylbenzyl, p-phenylphenacyl, p-bromophenacyl, 2,5-dimethoxyphenacyl and p-biphenylyloxycarbonylmethyl esters of each of the natural and synthetic prostaglandins specifically named hereinabove are prepared. Melting points of certain of these esters are set forth in the table below.

| Prostaglandin | p-Phenylbenzyl Ester | p-Phenylphenacyl Ester | p-Bromophenacyl Ester | 2,5-Dimethoxyphenacyl Ester | p-Biphenylyloxycarbonylmethyl Ester |
|---|---|---|---|---|---|
| $E_1$ | 105° | 112° | | | 105° |
| $E_2$ | 81° | 101° | 93° | 50° | 81° |
| $E_3$ | 52° | 57° | 55° | 45° | 61° |
| $F_{1\alpha}$ | 73° | 105° | 99° | 80° | 80° |
| $F_{2\alpha}$ | 85° | 111° | 96° | 56° | 83° |
| $F_{3\alpha}$ | 57° | 56° | 51° | 44° | 47° |

EXAMPLE 4

Reductive Splitting of the Phenacyl Esters 50 mg. of the $F_{2\alpha}$ -p-phenylphenacyl ester produced according to the procedure of Example 3 from prostaglandin-$F_{2\alpha}$ and p-phenylphenacylbromide, 200 mg. of zinc dust are agitated in 4 ml. of glacial acetic acid overnight at room temperature. Then, the mixture is filtered and evaporated to dryness under vacuum. The residue is filtered over a silica gel column with 5 g. of silica gel. Yield: 31 mg. of $F_{2\alpha}$ with chloroform/methanol (4+1).

Following the procedures of Examples 1–4, each of the specifically named prostanoic acid prostaglandins named herein in impure form, is esterified to form the p-phenylbenzyl, p-phenylphenacyl, p-bromophenacyl, 2,5-dimethoxyphenacyl and p-phenylphenylyloxycarbonylmethyl esters, each of which is then purified, e.g., by chromatography and/or fractional crystallization and the purified ester then regenerated, e.g., with zinc dust and glacial acetic acid, to regenerate in purified form the starting prostaglandin.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A crystalline prostanoic acid ester of the formula $$PG-CH_2-Y$$

wherein PG is the prostanoyloxy radical of prostaglandin $A_1$, prostaglandin $A_2$, prostaglandin $E_1$, prostaglandin $E_2$, prostaglandin $E_3$, prostaglandin $F_{1\alpha}$, prostaglandin $F_{2\alpha}$, prostaglandin $F_{3\alpha}$, prostaglandin $B_1$ or prostaglandin $B_2$ and Y is phenyl bearing one or two ring substituents selected from the group consisting of phenyl, alkoxy of 1–2 carbon atoms and halogen.

2. A prostanoic acid ester of claim 1 wherein —$CH_2$—Y is p-phenylbenzyl.

3. A compound of claim 1, prostaglandin $A_1$-p-phenylbenzyl ester.

4. A compound of claim 1, prostaglandin $F_{2\alpha}$-p-phenylbenzyl ester.

5. A compound of claim 1, prostaglandin $A_2$-p-phenylbenzyl ester.

6. A compound of claim 1, prostaglandin $E_2$-p-phenylbenzyl ester.

7. A compound of claim 1, prostaglandin $E_1$-p-phenyl-benzyl ester.

8. A compound of claim 1, prostaglandin $E_3$-p-phenyl-benzyl ester.

9. A compound of claim 1, prostaglandin $F_{1\alpha}$-p-phenylbenzyl ester.

10. A compound of claim 1, prostaglandin $F_{3\alpha}$-p-phenylbenzyl ester.

11. A compound of claim 1, prostaglandin $B_1$-p-phenylbenzyl ester.

12. A compound of claim 1, prostaglandin $B_2$-p-phenylbenzyl ester.

* * * * *

UNITED STATES PATENT AND TRADEMARK OFFICE
CERTIFICATE OF CORRECTION

PATENT NO. : 3,984,454
DATED : October 5, 1976
INVENTOR(S) : SKUBALLA ET AL.

It is certified that error appears in the above-identified patent and that said Letters Patent are hereby corrected as shown below:

Claim 1, line 2: Delete "ps".

Signed and Sealed this

Twenty-second Day of March 1977

[SEAL]

Attest:

RUTH C. MASON
*Attesting Officer*

C. MARSHALL DANN
*Commissioner of Patents and Trademarks*